(12) United States Patent
Iliyas et al.

(10) Patent No.: US 9,770,700 B2
(45) Date of Patent: Sep. 26, 2017

(54) REACTOR COMPRISING A PLASMA SOURCE AND A CATALYST COMPRISING A MESOPOROUS SUPPORT MATERIAL FOR THE PREPARATION OF ETHENE FROM METHANE

(71) Applicant: SAUDI BASIC INDUSTRIES CORPORATION, Riyadh (SA)

(72) Inventors: Abduljelil Iliyas, Riyadh (SA); Mohamed Sabri Abdelghani, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/913,035

(22) PCT Filed: Aug. 20, 2014

(86) PCT No.: PCT/IB2014/063991
§ 371 (c)(1),
(2) Date: Feb. 19, 2016

(87) PCT Pub. No.: WO2015/025284
PCT Pub. Date: Feb. 26, 2015

(65) Prior Publication Data
US 2016/0199806 A1   Jul. 14, 2016

Related U.S. Application Data

(60) Provisional application No. 61/869,131, filed on Aug. 23, 2013.

(51) Int. Cl.
| | |
|---|---|
| *B01J 23/44* | (2006.01) |
| *B01J 21/12* | (2006.01) |
| *C07C 2/00* | (2006.01) |
| *B01J 19/08* | (2006.01) |
| *C01B 3/26* | (2006.01) |
| *C07C 2/76* | (2006.01) |
| *C08F 110/02* | (2006.01) |
| *C07C 2/84* | (2006.01) |
| *C10G 50/00* | (2006.01) |

(52) U.S. Cl.
CPC ............. *B01J 19/088* (2013.01); *C01B 3/26* (2013.01); *C07C 2/76* (2013.01); *C07C 2/84* (2013.01); *C08F 110/02* (2013.01); *C10G 50/00* (2013.01); *B01J 2219/0805* (2013.01); *B01J 2219/0875* (2013.01); *B01J 2219/0892* (2013.01); *B01J 2219/0894* (2013.01); *B01J 2219/0896* (2013.01); *B01J 2219/0898* (2013.01); *C01B 2203/107* (2013.01); *C01B 2203/1058* (2013.01); *C01B 2203/1082* (2013.01); *C01B 2203/1241* (2013.01); *C07C 2523/44* (2013.01); *C07C 2529/74* (2013.01)

(58) Field of Classification Search
CPC .. C07C 2/84; C07C 2/82; C07C 11/04; C07C 2521/08; C07C 2523/44; C07C 2523/50; C07C 2523/755
See application file for complete search history.

(56) References Cited

U.S. PATENT DOCUMENTS

| 4,574,038 A | * | 3/1986 | Wan ........................ B01J 19/126 204/157.15 |
| 4,769,507 A | * | 9/1988 | Murib ........................ C07C 2/84 585/417 |
| 4,918,257 A | * | 4/1990 | Murib ........................ C07C 2/84 585/500 |
| 5,012,028 A | * | 4/1991 | Gupta ...................... B01J 8/0242 585/500 |
| 5,015,349 A | * | 5/1991 | Suib ........................ B01J 19/126 204/157.15 |
| 2002/0034471 A1 | * | 3/2002 | Jacobsen ............... B01J 29/0308 423/700 |
| 2010/0166633 A1 | * | 7/2010 | Wu ...................... B01D 53/8687 423/245.3 |
| 2012/0041246 A1 | | 2/2012 | Scher et al. |
| 2012/0065412 A1 | | 3/2012 | Abdallah et al. |
| 2012/0237439 A1 | * | 9/2012 | Rouleau ............... B01J 29/0308 423/628 |
| 2014/0336432 A1 | * | 11/2014 | Bao ........................... C07C 2/84 585/417 |
| 2015/0050191 A1 | * | 2/2015 | Li ............................. A61L 9/22 422/122 |

FOREIGN PATENT DOCUMENTS

| CN | 1163254 A | * 10/1997 | ............... C07C 2/80 |
| CN | 1696084 A | * 11/2005 | ............... C07C 2/84 |

(Continued)

OTHER PUBLICATIONS

Shi et al. CN 101204589 A, Jun. 25, 2008; machine translation.*
CN 1696084 A; Bao et al. Nov. 2005; machine translation.*
CN 101288851 A; Shen et al. Oct. 2008; machine translation.*
French Patent No. 2873306; Date of Publication: Jan. 27, 2006; Abstract Only, 2 pages.
International Search Report for International Application No. PCT/1132014/063991; dated Dec. 8, 2014; 2 pages.

(Continued)

*Primary Examiner* — Rip A Lee
(74) *Attorney, Agent, or Firm* — Cantor Colburn LLP (57) ABSTRACT

The invention relates to a reactor comprising a plasma source and a catalyst comprising a mesoporous support. The invention also relates to a process comprising feeding methane to said reactor in order to obtain one or more of ethene, hydrogen and carbon as well as downstream products derived from ethene thus obtained. The invention relates to a reactor comprising as reactor parts: a. a housing and in said housing; b. a plasma source; and c. a catalyst, wherein said catalyst comprises as catalyst parts: i) a mesoporous support; ii) a metal selected from the group Pd, Ni, Ag or at least two thereof, wherein the metal is carried by said mesoporous support; wherein at least a part of said plasma source is located in said housing upstream of said catalyst.

14 Claims, 7 Drawing Sheets

(56) References Cited

FOREIGN PATENT DOCUMENTS

| | | | | |
|---|---|---|---|---|
| CN | 1861519 | A | 11/2006 | |
| CN | 101204589 | A * | 6/2008 | ............ A61L 9/014 |
| CN | 101288851 | A * | 10/2008 | ............ B01J 29/00 |
| CN | 101352685 | A * | 1/2009 | ............ B01J 23/755 |
| FR | 2873306 | A1 | 1/2006 | |
| JP | 2008049280 | A | 3/2008 | |
| WO | 9316021 | A1 | 8/1993 | |
| WO | 2012094743 | A1 | 7/2012 | |

OTHER PUBLICATIONS

Written Opinion of the International Searching Authority for International Application No. PCT/IB2014/063991; dated Dec. 8, 2014; 5 pages.
Chinese U.S. Pat. No. 1163254; Date of Publication: Oct. 29, 1997; Abstract Only; 1 page.
Chinese U.S. Pat. No. 1861519: Date of Publication: Nov. 15, 2006; Abstract Only; 1 page.
Japanese U.S. Pat. No. 2008049280; Date of Publication: Mar. 6, 2008; Abstract Only; 2 pages.
Chinese Patent No. 1696084; Date of Publication: Nov. 11, 2005; Abstract Only; 1 page.

* cited by examiner

REACTOR COMPRISING A PLASMA SOURCE AND A CATALYST COMPRISING A MESOPOROUS SUPPORT MATERIAL FOR THE PREPARATION OF ETHENE FROM METHANE

CROSS REFERENCE TO RELATED APPLICATIONS

This application is a 371 of International Application No. PCT/IB2014/063991, filed Aug. 20, 2014, which claims priority to U.S. Application No. 61/869,131, filed Aug. 23, 2013, both of which are incorporated herein by reference in their entirety.

TECHNICAL FIELD

The invention relates to a reactor comprising a plasma source and a catalyst comprising a mesoporous support material. The invention also relates to a process comprising feeding methane to said reactor in order to obtain one or more of ethene, hydrogen or carbon or downstream products derived from those products.

BACKGROUND

Ethene has for a long time been one of the most desirable substances derived from petrochemical fuels. Its use in the production of polythene and its derivatives contributes to its high economic value. One route to the preparation of ethene is the cracking of higher petrochemical fractions containing more than 2 carbon atoms. A further route to the preparation of ethene, which has for a long time been the subject of intense research, is from methane. The demand still remains in the state of the art for improved processes for the preparation of ethene from methane, especially for processes with low energy costs, long catalyst lifetimes, high yield and high production rate.

SUMMARY

A reactor comprises, as reactor parts: a. a housing; and in said housing; b. a plasma source; and c. a catalyst, wherein said catalyst comprises as catalyst parts: i) a mesoporous support; ii) a metal selected from the group Pd, Ni, Ag or at least two thereof, wherein the metal is carried by said mesoporous support; wherein at least a part of said plasma source is located in said housing upstream of said catalyst.

A process for the preparation of a product selected from ethane and hydrogen or both, comprises: i. feeding methane into a reactor according to any of the preceding claims; and ii. reacting the methane to furnish the product in the reactor.

The above described and other features are exemplified by the following figures and detailed description.

BRIEF DESCRIPTION OF THE DRAWINGS

Refer now to the figures, which are exemplary embodiments, and wherein like elements are numbered alike and which are presented for the purposes of illustrating the exemplary embodiments disclosed herein and not for the purposes of limiting the same.

DETAILED DESCRIPTION

The present invention is generally based on overcoming at least one of the problems encountered in the state of the art in relation to the reaction of methane to give at least one product selected from ethene, hydrogen and carbon, preferably ethene, or downstream products derived therefrom, preferably polythene or its derivatives.

More specifically, the present invention is further based on providing a reactor and a process for a reaction which has a low energy cost, a high catalyst lifetime, a high overall efficiency, and a fast output rate.

Another desire is to provide an efficient and sustainable ethene source for producing downstream products and shaped bodies.

A contribution to solving at least one of the problems disclose herein is made by the subject matter of the category forming claims of the present invention. A further contribution is made by the subject matter of the dependent claims of the present invention which represent specific embodiments of the present invention.

A contribution to achieving at least one of the above-mentioned problems is made by a reactor comprising as reactor parts:
  a. a housing; and in said housing
  b. a plasma source; and
  c. a catalyst, wherein said catalyst comprises as catalyst parts:
    i) a mesoporous support;
    ii) a metal selected from the group Pd, Ni, Ag or at least two thereof, wherein the metal is carried by said mesoporous support;
wherein at least a part of said plasma source is located in said housing upstream of said catalyst.

In one embodiment of the reactor according to the invention, the mesoporous support has a $d_{50}$ value for pore diameter of about 2 to about 50 nanometers (nm), preferably about 10 to about 50 nm, more preferably about 20 to about 50 nm.

In one embodiment of the reactor according to the invention, the mesoporous support is mesoporous silica.

In one embodiment of the reactor according to the invention, the mesoporous support has a surface area to mass ratio of about 10 to about 1500 square meters per gram ($m^2/g$), preferably about 500 to about 1200 $m^2/g$, more preferably about 800 to about 1000 $m^2/g$.

In one embodiment of the reactor according to the invention, the metal in the catalyst is Pd.

In one embodiment of the reactor according to the invention, the mesoporous support is selected from one of the following families: SBA-15 (commercially available from ACS materials), SBA-16 (commercially available from ACS materials), MCM-48 (commercially available from ACS materials), MCM-41 (commercially available from Sigma Aldrich), or a combination of at least two thereof, preferably SBA-15.

In one embodiment of the reactor according to the invention, the catalyst comprises Pd supported on SBA-15, SBA-16, MCM-48, MCM-41, or a combination of at least two thereof, preferably Pd supported on SBA-15.

In one embodiment of the reactor, the mesoporous support is SBA-15.

In one embodiment of the reactor according to the invention, there is at least partial spatial overlap of the plasma source and the catalyst.

In one embodiment of the reactor according to the invention, there is no spatial overlap of the plasma source and the catalyst.

A contribution to solving at least one of the problems disclosed herein is made by a process for the preparation of a product selected from ethene and hydrogen or both, preferably ethene, comprising:
  i. feeding methane into a reactor according to the invention; and
  ii. reacting the methane to furnish the product in the reactor.

A contribution to solving at least one of the problems disclosed herein is made by a product selected from the group consisting of ethene and hydrogen or both, obtained by a process according to the invention.

In one embodiment of the process according to the invention, methane is fed to the reactor mixed with a carrier gas selected from the group consisting of $N_2$, Ar, or He, or a combination of at least two thereof, preferably $N_2$.

In one embodiment of the process according to the invention, at least one, or two or more, or all, of the following conditions is satisfied:
  a. the maximum temperature within the reactor is about 0 to about 200° C., preferably about 30 to about 180° C., most preferably about 50 to about 150° C.;
  b. the partial pressure of methane fed to the reactor is about 0.05 MegaPascals (MPa) to about 0.2 MPa (about 0.5 to about 2 atmospheres (atm.)), or about 0.08 MPa to about 0.15 MPa (about 0.8 to about 1.5 atm.), or about 0.1 MPa to about 10 MPa (about 10 to about 100 atm.).
  c. the power density of the plasma source output, expressed as the power of the plasma source divided by the flow rate of the methane, is about 0.1 to 30 kiloJoules per gram (kJ/g), preferably about 1 to about 20 kJ/g, more preferably about 5 to about 10 kJ/g.
  d. the partial pressure of the carrier gas is about 0.1 to about 10 atm., or about 0.5 to about 5 kiloWatts per gram (kW/g), or about 0.1 to about 100 kW/g.

Preferred aspects of this embodiment correspond to the following combinations expressed as the letter combinations a, b, c, d, ab, ac, ad, bc, bd, cd, abc, abd, acd, bcd, or abcd.

A contribution to solving at least one of the problems disclosed herein is made by a process for the preparation of a downstream product comprising the following steps:
  i. preparation of ethene by a process according to the invention; and
  ii. reaction of the ethene to form the downstream product.

A contribution to solving at least one of the problems disclosed herein is made by a downstream product, preferably a polymer, preferably polythene or a derivative thereof, preferably in the form of a shaped body, obtained by a process according to the invention.

In one embodiment of the process according to the invention, the downstream product is a polymer.

In one embodiment of the process according to the invention, the downstream product is a polythene.

In one embodiment of the process according to the invention, the downstream product is converted into a shaped body.

Reaction

A contribution to solving at least one of the problems disclosed herein is made by a reaction of methane to provide one or more products selected from the group consisting of carbon, ethene or hydrogen, preferably ethene. Preferred reactions are those with a low energy cost, a high catalyst lifetime, high yield, in particular a high selectivity of desired products over by-products, and a fast output rate.

In one embodiment of the invention, ethene is desired as a product and a high selectivity of ethene over other products, in particular ethene, ethane and carbon, is preferred.

In one embodiment of the invention, carbon is desired as a product and it is preferred for the reaction to give a high selectivity of the specific form or forms of carbon, preferably carbon nanotubes, fullerenes or carbon nano-sheets, or a combination of at least two thereof.

In one embodiment of the invention both ethene and hydrogen are desired as products and these two products are separated from each other following their formation in the reactor.

Plasma Source

Preferred plasma sources are devices which are capable of breaking at least one C—H bond in methane as part of the reaction according to the invention. It is further preferred for the selection of plasma source to contribute to advantageous characteristics of the reaction according to the invention.

Plasma sources are known to the skilled person. Any plasma source known to the skilled person and which he considers to be suitable in the context of the invention can be employed, such as non-thermal plasma, corona discharge, dielectric barrier discharge, microwave discharge and normal glow discharge. Non-thermal plasma sources are preferred in the context of the invention, preferably those based on an AC discharge. In the context of non-thermal plasma sources, it is preferred for no heating of the reactant gas to occur before exposure to the plasma source.

As well as through selection of an appropriate plasma source, the skilled person can adjust settings of the plasma source, such as frequency and voltage, in any way he sees fit, in order to increase favourable characteristics of the reaction according to the invention. It is particularly preferred in the context of the invention for the plasma source to draw a low specific power. Useful information in this regard can be taken from the paper "Hydrogen Manufacturing Using Low Current, Non-thermal Plasma Boosted Fuel Converters" of L. Bromberg, D. R. Coh, A. Rabinovich and N. Alexeev, published in the Proceedings of the Symposium on ENERGY FOR THE 21$^{ST}$ CENTURY: HYDROGEN ENERGY, April 2001 San Diego, Calif., which is incorporated in this patent application in its entirety.

In one embodiment of the invention, the specific power consumption of the plasma source, expressed as the electrical power drawn per unit mass of methane flowing into the reactor, is about 0.1 to about 30 kJ/g, or about 1 to about 20 kJ/g, or about 5 to about 15 kJ/g.

Catalyst

Preferred catalysts are those which catalyse the reaction according to the invention, particularly those which contribute to an increase in energy efficiency, an increase in reaction rate and/or an increase in yield/selectivity of products. Preferred catalysts are those which are suited to catalysing the reaction according to the invention when provided as part of a reactor with a plasma source at least partially upstream of them.

It is preferred according to the invention for the catalyst to comprise a catalyst metal present on a mesoporous support material.

It is preferred according to the invention for the ratio by weight of metal catalyst to mesoporous support material in the catalyst to be about 1:10 to about 1:1000, or about 1:50 to about 1:500, or about 1:100 to about 1:200.

Catalyst Metal

Preferred metals comprised by the catalyst according to the invention are those which catalyse the reaction according to the invention and contribute to advantageous characteristics of the reaction according to the invention.

The term catalyst metal, as used in this patent application refers to those substances which fulfil the above mentioned role of catalyst. In addition to those materials consisting of a pure element which would traditionally be considered a metallic element, the term catalyst metal as used in this patent extends to other elements, alloys or mixtures of elements, or compounds, which fulfil the role of catalyst as described above. Catalyst metals are well known to the skilled person. Any catalyst metal which is known to the skilled person and which he considers to be suitable to be comprised in the catalyst according to the invention can be employed.

Preferred catalyst metals in the context of the invention are transitions metals, alloys comprising transition metals, or combinations of at least thereof. Preferred transition metals in this context are Ni, Cu, Pd, Ag, Pt and Au, particularly preferably Ni, Ag or Pd or at least two thereof. The preferred catalyst metal is Pd.

Mesoporous Support Material

Preferred mesoporous supports according to the invention are those which, when used as support for the catalyst metal according to the invention, contribute to the catalysis of the reaction and to favourable characteristics of the reaction according to the invention. Mesoporous support materials are well known to the skilled person and any mesoporous support material which he considers suitable in the context of the invention may be employed. Preferred mesoporous support materials in the context of the invention have an average $d_{50}$ for pore size of about 2 to about 50 nm, preferably about 10 to about 50 nm, more preferably about 20 to about 50 nm. Pores in mesoporous materials are frequently anisotropic. In such a case, pore size is understood to mean the smallest dimension.

The term microporous is often used to refer to materials with a pore size of less than 2 nm. It is preferred according to the invention that the mesoporous material have a pore size equal to or greater than 2 nm. It is therefore preferred that the mesoporous material not be microporous. The term macroporous is often used to refer to materials with a pore size greater than 50 nm. It is preferred according to the invention that the mesoporous material have a pore size equal to or less than 50 nm. It is therefore preferred that the mesoporous material not be macroporous.

Preferred mesoporous support materials in the context of the invention have a large specific surface area, preferably above about 100 $m^2/g$, or above about 500 $m^2/g$, or above about 800 $m^2/g$. Values for specific surface area of above up to about 10,000 $m^2/g$ or less have been employed.

The mesoporous material can consist of any material known to the skilled person and which he considers to be suitable in the context of the invention, such as zeolites or silica. The preferred mesoporous material is silica.

Mesoporous silica is well known to the skilled person and he can employ any mesoporous silica material which he deems suitable in the context of the invention. Preferred mesoporous support materials are those with at least partial long-range ordering, which can be selected by the skilled person in order to achieve the desired advantageous properties of the catalyst system. Preferred pore structures of the catalyst support materials can be 1d, 2d or 3d, this dimensionality expressing the number of special dimensions in which pores have a spatial extension of 1 μm or longer. Structures which can be formed by channels in the mesoporous material can be, for example, linear parallel channels, laminas, 3d interconnected structures, 3d cages, single cages. Channels can be straight, curved, isolated, interconnected or connected by secondary interconnections.

In connection with mesoporous materials, in particular with mesoporous silica, it is common to classify materials according to their characteristic long range ordering, this designation of long range ordering commonly neglecting local asymmetry, silica commonly being essentially amorphous locally on the pore walls. Preferred mesoporous silica materials according to the invention are those of the M41S family. Some preferred long range symmetries are hexagonal or cubic.

Some preferred families of mesoporous silica are the MCM, SBA, MSU, TUD, KSW or FSM families. Some preferred structures selected from these families are MCM-41, SBA-15, SBA-16, TUD-1, HMM-33, FSM-16, MCM-48, preferably MCM-41, MCM-48, SBA-15 or SBA-16, more preferably SBA-15.

In addition to long range structure, further properties of the mesoporous materials, such as pore dimensions, channel length, channel thickness, channel breadth, or interstitial or integral impurities, can be tuned by the skilled person to bring about advantageous properties in the of the reaction according to the invention. Syntheses for mesoporous materials are well known to the skilled person as are techniques for modifying macroscopic, microscopic and symmetry properties. The skilled person may employ any technique he sees fit to tune the properties of the mesoporous material such as modifying the identity or proportions of reactants, modifying reaction conditions such as temperature or pressure, modifying surfactants used, particularly by modifying surfactant chain length, introducing impurities etc. Further details of the syntheses of SBA-15 and MCM-41 can be found in "SBA-15 templated-ordered mesoporous carbon: effect of SBA-15 microporosity" (Yong Yang and Abdelhamid Sayari, 2005, Studies in Surface Science and Catalysis 156, pp 543-550) and "Catalysts from MCM-41: framework modification, pore size engineering, and organic-inorganic hybrid materials" (G. K. Chuah, X. P. Zhan, S. Jaenicke, Journal of Molecular Catalysis A: Chemical 181 (2002) 25-31) respectively, the content of these two documents being incorporated in this application in their entirety.

A number of techniques for introduction of catalyst metal into a mesoporous support material are known to the skilled person and any technique which he considers appropriate may be employed. The catalyst metal may be introduced into the mesoporous support material in situ during the preparation of the mesoporous support material, or in a subsequent step, preferably in a subsequent step.

In one embodiment, the metal catalyst is introduced in situ during the preparation of the mesoporous support material. Such a procedure can include A. Combining the following reactants:
   a. reactants for mesoporous support material, preferably the following:
      i. aqueous acidic solution, preferably $H_2SO_4$;
      ii. silica source, preferably $Na_2SiO_4$;
      iii. surfactant, preferably a triblock copolymer, preferably a triblock polymer based on poly(ethylene glycol)-poly(propylene glycol)-poly(ethylene glycol), preferably $HO(CH_2CH_2O)_{20}(CH_2CH(CH_3)O)_{70}(CH_2CH_2O)_{20}H$, which is commercially available, for instance from BASF SE under the tradename Pluronic P123;
   b. source of catalyst metal, preferably an aqueous metal solution, preferably comprising palladium cations.
B. Stirring and aging, preferably at a temperature of about 10° C. to about 70° C., more preferably about 20° C. to about 60° C., more preferably about 30° C. to about 50° C., preferably for a period of about 20 to about 60 hours, more preferably about 30 to about 55 hours, more preferably about 36 to about 48 hours.
C. Filtering, washing and drying, preferably at a temperature of about 60° C. to about 100° C., more preferably about 60° C. to about 100° C., most preferably about 60° C. to about 100° C., preferably for a duration of about 10 to 40 hours, more preferably about 15 to 35 hours, most preferably about 20 to 30 hours.
D. Calcination, preferably for a duration of about 30 minutes to about 3 hours, more preferably about 40 minutes to about 2 hours, most preferably about 50 minutes to about 90 minutes, preferably at a temperature of about 400° C. to about 700° C., more preferably about 450° C. to about 650° C., most preferably about 500° C. to about 600° C. to obtain the mesoporous support material with catalyst metal.

In another embodiment, the metal catalyst is introduced subsequent to the synthesis of the mesoporous support material. Such a procedure might look as follows.
A. Combining the following reactants:
   a. reactants for mesoporous support material, preferably the following:
      i. aqueous acidic solution, preferably $H_2SO_4$;
      ii. silica source, preferably $Na_2SiO_4$;
      iii. surfactant, preferably a triblock copolymer, preferably a triblock polymer based on poly(ethylene glycol)-poly(propylene glycol)-poly(ethylene glycol), preferably $HO(CH_2CH_2O)_{20}(CH_2CH(CH_3)O)_{70}(CH_2CH_2O)_{20}H$, which is commercially available, for instance from BASF SE under the tradename Pluronic P123;
B. Stirring and aging, preferably at a temperature of about 10° C. to about 70° C., more preferably about 20° C. to about 60° C., more preferably about 30° C. to about 50° C., preferably for a period about 20 to about 60 hours, more preferably about 30 to about 55 hours, more preferably about 36 to about 48 hours.
C. Filtering, washing and drying, preferably at a temperature of about 60° C. to about 100° C., more preferably about 60° C. to about 100° C., most preferably about 60° C. to about 100° C., preferably for a duration about 10 to 40 hours, more preferably about 15 to 35 hours, most preferably about 20 to 30 hours.
D. Calcination, preferably at a temperature of about 400° C. to about 700° C., more preferably about 450° C. to about 650° C., most preferably about 500° C. to about 600° C., to obtain SBA-15.
E. Introduction of a metal source, preferably a Pd source, preferably palladium acetylacetone, preferably in benzene solution, to the SBA-15.
F. Stirring, preferably for a during of about 30 minutes to about 3 hours, more preferably about 40 minutes to about 2 hours, most preferably about 50 minutes to about 90 minutes, preferably at a temperature of about 10° C. to about 40° C., more preferably about 15° C. to about 35° C., most preferably about 20° C. to about 30° C.
G. Drying and calcination, preferably for a duration of about 30 minutes to about 3 hours, more preferably about 40 minutes to about 2 hours, most preferably about 50 minutes to about 90 minutes, preferably at a temperature about 400° C. to about 700° C., more preferably about 450° C. to about 650° C., most preferably about 500° C. to about 600° C. to obtain the mesoporous support material with catalyst metal.

Figure 7:
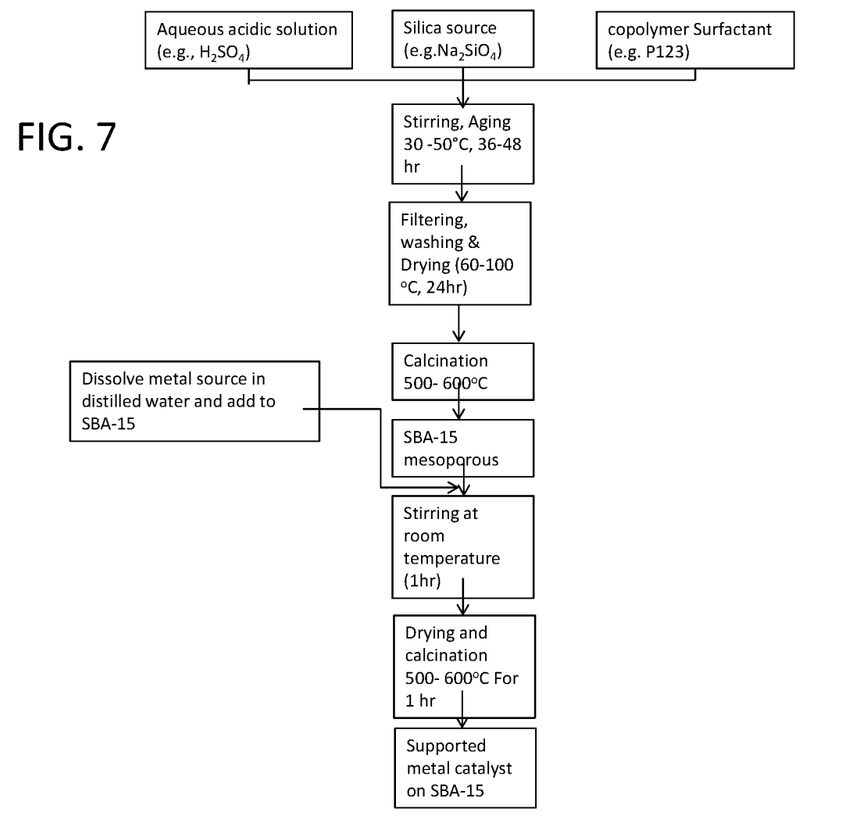
FIG. 7 shows a process flow for an example preparation of a mesoporous support material with catalyst metal.

An example procedure for the preparation of the mesoporous support material SBA-15 and a subsequent step to incorporate a catalyst metal is shown schematically in FIG. 7.

Reactor Configuration

Preferred reactors are flow reactors which facilitate the reaction according to the invention and particularly those which contribute to advantageous characteristics such as low energy cost, a high catalyst lifetime, high yield, in particular a high selectivity of ethene over ethene and other by-products, and a fast output rate. Reactor configurations are well known to the skilled person and he may select characteristics of the reactor which he deems suitable in the context of the invention.

Preferred reactors according to the invention are those which comprise the following reactor components:
   1. a plasma source; and
   2. a catalyst situated such that at least part of the plasma source is upstream of the catalyst.

In one embodiment of the invention, there is at least partial spatial overlap of the plasma source and the catalyst. In a further embodiment of the invention, there is no spatial overlap of the plasma source and the catalyst, the plasma source in its entirety being situated upstream of the catalyst in its entirety.

Reference to a housing in the context of the invention designates one or more components of the flow reactor situated in flow connection, preferably air-tight with an inlet and an outlet. This term is equally used in the context of the invention to refer to what could be identified as a single chamber or what might also be better identified as a number of interconnected modular chambers. In one embodiment, at least two reactor components are provided within a shared housing. In another embodiment of the system, at least two modular housings are provided and connected via connectors.

The skilled person is aware of favourable characteristics for reactor components, such as size, shape, or material, and can modify these characteristics as he sees fit in the context of the invention. Preferred plasma reactors are those which favour energy efficiency, high conversion rate and proportion of reactant into reactive species and eventually product and which allow a fast flow rate. Preferred catalysis reactors are those which favour energy efficiency, high reaction yield, fast reaction rate and which allow for a fast flow rate. Arrangements of the catalysis reactor which maximise contact of reactants with the surface area of the catalyst are preferred, such as a tube packed with catalyst.

Further to comprising a plasma source and a catalyst, reactors according to the invention may comprise further reactor components which may be situated partially or entirely before or after the plasma source and/or the catalysts and/or each other so as to provide a partial or full overlap or no overlap. Further reactor components may be present as connected modular units, or together in a shared container with each other and/or the plasma source and catalyst. Some examples of preferred additional reactor components are given in the following embodiments.

In one embodiment, the reactor further comprises one or more reactant source components, preferably situated at least partially, preferably entirely before the plasma source. Where a reactant source component is present, the reactor considered as a whole facilitates a reaction starting from pre-reactants. Preferred reactant sources might be those in which, for example, higher petrochemical fractions are cracked or another process is carried out which produces methane as a product or as a by-product, and/or a component which separates methane from a mixture.

In one embodiment, the reactor further comprises one or more pre-treatment components, preferably situated at least partially, preferably entirely before the plasma source and preferably at least partially, preferably entirely after a reactant source if one is present. Preferred pre-treatment components are those which, for example, remove unwanted ingredients in the reactant such as oxygen and/or water, introduce desirable constituents or carrier gases, or modify temperature, vibrational, rotational, electronic or other excitation state.

In one embodiment, the reactor further comprises one or more measurement and/or analysis components. Such components preferably serve to measure temperature, pressure, material proportion etc., and are preferably coupled to controls for other components in order to maximise reaction characteristics through feedback control.

In one embodiment, the reactor further comprises one or more intermediate treatment components, preferably situated at least partially, preferably entirely, after the plasma source, and preferably at least partially, preferably entirely, before the catalyst. In the case that an intermediate treatment component is present, it preferably prepares the flow of material for the catalyst by removing impurities, particularly carbon and/or other materials which might impair and/or reduce the lifetime of the catalyst, or by modifying the temperature, pressure or other properties of the materials in order to bring about favourable conditions for the catalysis reaction. In one embodiment, the reactor comprises a carbon scrubber at least partially upstream of the catalyst.

In one embodiment, the reactor further comprises one or more post-treatment and/or distillation components which are preferably situated at least partially, preferably entirely, downstream of the catalyst. In the case that a post-treatment/distillation component is present, it preferably removes undesired by-products and/or separates the desired products from each other.

In one embodiment, the reactor further comprises one or more further downstream reactor components which are preferably situated at least partially, preferably entirely downstream of all of the above mentioned reactor components. In the case where such a further downstream reactor component is present, it preferably facilitates the reaction of the products of the reaction according to the invention to provide downstream products such as polymers, preferably polythene or its derivatives, or hydrogenation products.

Process

Preferred processes which may be carried out in the reactor according to the invention are those which provide at least one of ethene, carbon or hydrogen. The skilled person is well versed in the many ways to improve chemical reactions and can make any amendments such as to the reaction conditions or to the reactants, in order to bring about advantageous properties of the reaction.

Temperatures for the reaction may be selected by the skilled person in order to improve advantageous characteristics of the reaction. The temperature of reactants fed to the reactor and thus the temperature within the reactor are preferably suited to the catalyst employed, preferably a relatively low temperature. In one embodiment it is preferred that the reactant material by fed into the reactor at a temperature of about 0 to about 200° C. or about 30 to about 180° C., or about 50 to about 150° C.

Absolute pressures within the reactor and for reactants at the point of entry into the reactor may be selected by the skilled person in order to improve advantageous characteristics of the reaction. In one embodiment, it is preferred according to the invention, for reasons of economy, for pressures close to atmospheric pressure to be employed in the reactor. In one embodiment, it is preferred for the average pressure in the reactor to be about 0.01 MPa to about 1.0 MPa (about 0.1 to about 10 atm.), or about 0.05 MPa to about 0.5 MPa (about 0.5 to about 5 atm.), or about 0.08 MPa to about 0.15 MPa (about 0.8 to about 1.5 atm.).

Identity and proportions of materials fed to the reactor may be selected by the skilled person in order to improve advantageous characteristics of the reaction according to the invention. In one embodiment, a carrier gas is employed, preferably one or more selected from the group consisting of argon, neon, nitrogen, or helium, preferably nitrogen. Other constituents may be present as a mixture with the reactants in order to improve the reaction or for convenience. In one embodiment, the reactants are fed to the reactor in the form of natural gas. In one embodiment the reactants comprises methane in an amount of about 70 to about 99 weight percent (wt. %), optionally ethane in an amount of about 0 to about 20 wt. %, optionally propane in an amount of about 0 to about 20 wt. %, and optionally butane in an amount of about 0 to about 20 wt. %. In one embodiment, it is preferred that the reactant material have a low concentration of oxygen containing compounds, preferably less than 0.1 wt. %, or less than 0.01 wt. %, or less than 0.001 wt. %. Concentrations less than as low as 0.00001 wt. % or above have been employed. In one embodiment, it is preferred that the reactant material have a low concentration of oxygen, preferably less than 0.1 wt. %, or less than 0.01 wt. %, or less than 0.001 wt. %. Concentrations less than as low as 0.00001 wt. % or above have been employed. In one embodiment, it is preferred that the reactant material have a low concentration of water, preferably less than 0.1 wt. %, or less than 0.01 wt. %, or less than 0.001 wt. %. Concentrations less than as low as 0.00001 wt. % or above have been employed. In one embodiment, it is preferred that the content of methane in the reactants be high, preferably in an amount of about 50 to about 100 wt. %, or in an amount of about 80 to about 100 wt. %, or in an amount of about 95 to about 100 wt. %.

Downstream Products

In one embodiment of the invention, the process according to the invention for the preparation of ethene is coupled to further subsequent reactions in order to obtain downstream products. Preferred downstream products are those obtained from polymerisation reactions, hydrogenation reactions, halogenation reactions, and other chemical functionalization reactions, preferably polymerisation reactions. Preferred monomeric downstream products are vinyl chloride monomer (VCM), ethylene glycol monomer (MEG), ethylene oxide (EO), acrylonitrile, butadiene, styrene, vinyl acetate monomer (VAM). Preferred oligomers are olefins, preferably linear olefins, preferably alpha olefins, preferably linear alpha olefins, such as 1-butene, 1-hexene, 1-octene, 1-decene, 1-dodecene, 1-tetradecene, 1-hexadecene or 1-octadecene. Preferred polymerisation reactions can be mono-polymerization reactions or co-polymerization reactions. Preferred polymerisation products are polythene, substituted polythene, polythene derivatives, polyvinyl chloride, polyethylene glycol (PEG), acrylonitrile butadiene styrene (ABS), polyvinyl acetate, poly olefins, preferably poly alpha olefins (PAO), styrene butadiene rubber (SBR), and other polymers comprising at least one of the above described monomers. Preferred polymers are polythene or polythene derivatives. Preferred forms of polythene and its derivatives are ultra-high-molecular-weight polyethylene (UHMWPE), ultra-low-molecular-weight polyethylene (ULMWPE or PE-WAX), high-molecular-weight polyethylene (HMWPE), high-density polyethylene (HDPE), high-density cross-linked polyethylene (HDXLPE), cross-linked polyethylene (PEX or XLPE), medium-density polyethylene (MDPE), linear low-density polyethylene (LLDPE), low-density polyethylene (LDPE), or very-low-density polyethylene (VLDPE), chlorinated polyethylene (CPE), or combinations of at least two thereof, preferably HDPE, LLDPE or LDPE. Preferred functionalization products are aromatic or non-aromatic compounds, saturated or unsaturated compounds, ketones, aldehydes, esters, amides, amines, carboxylic acids, alcohols etc.

In one embodiment according to the invention, the downstream products are further processed, particularly in the case where the downstream product is a polymer, particularly when it is polythene or a derivative thereof. In one embodiment, this further processing preferably involves formation of shaped objects such as plastic parts for electronic devices, automobile parts, such as bumpers, dashboards, or other body parts, furniture, or other parts or merchandise, or for packaging, such as plastic bags, film, or containers.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Figure 1:
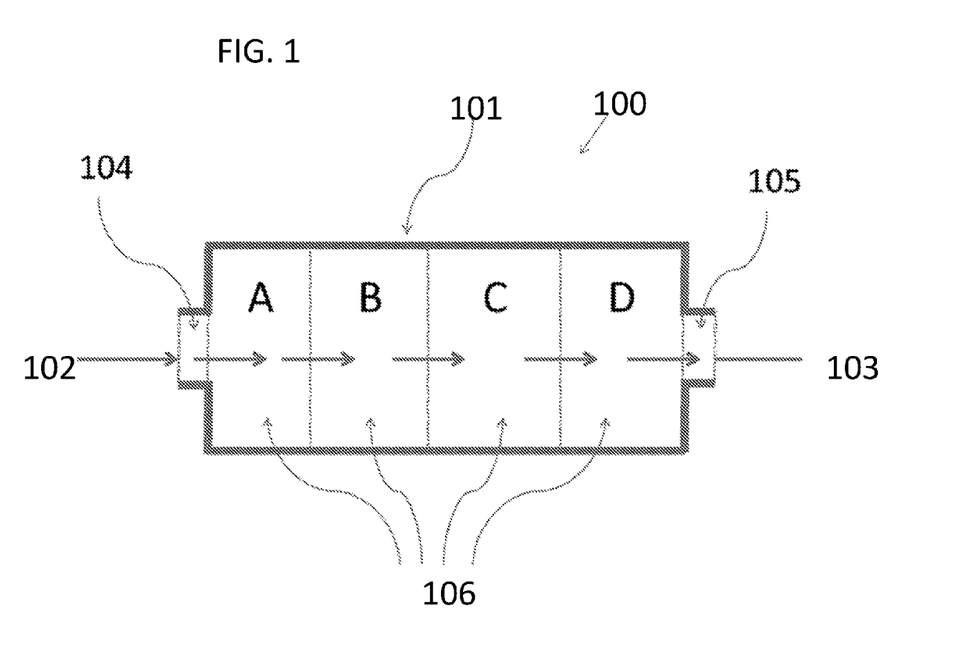
FIG. 1 shows a schematic view of a reactor in which several reactor components are provided in a single housing.

FIG. 1 shows a schematic view of a reactor 100 in which a number of reactor components 106 are provided in a single reactor housing 101. For illustrative purposes, four reactor components 106 have been shown and labelled generically as A, B, C and & D. According to the invention, at least one of the reactor components 106 is a plasma source 309, preferably non-thermal plasma source, and at least one of the reactor components 106 is a catalyst 310 comprising a catalyst metal, preferably Pd, on a mesoporous catalyst support material, preferably mesoporous silica, at least part of the plasma source 309 being situated upstream of the catalyst 310. Reactants 102 enter the reactor via the reactor entrance 104 and the reaction material passes through each of the reactor components 106 before products 103 exit via the reactor exit 105. Apart from the reactor entrance 104 and the reactor exit 105, it is preferred for the reactor housing 101 to be airtight.

Figure 2:
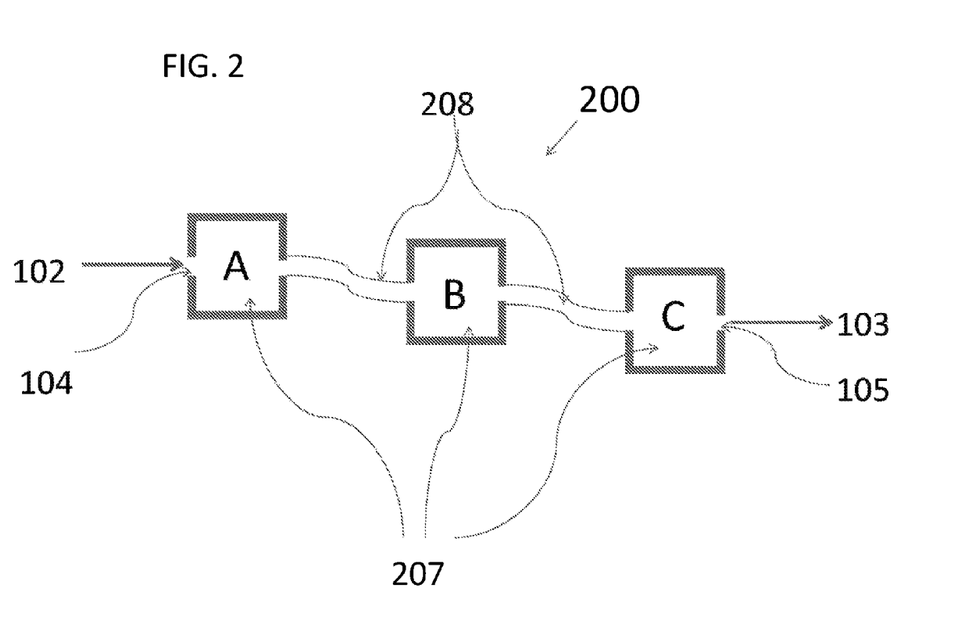
FIG. 2 shows a schematic view of a reactor in which several reactor components are provided as connected modules.

FIG. 2 shows a schematic view of a reactor 200 in which a number of modular reactor components 106 are provided in separate housings 207, connected in flow communication by connections 208. For illustrative purposes, three reactor components 106 have been shown and labelled generically as A, B and C. According to the invention, at least one of the reactor components 106 is a plasma source 309, preferably non-thermal plasma source, and at least one of the reactor components 106 is a catalyst 310 comprising a catalyst metal, preferably Pd, on a mesoporous catalyst support material, preferably mesoporous silica, the plasma source 309 being situated upstream of the catalyst 310. Reactants 102 enter the reactor via the reactor entrance 104 and the reaction material passes through each of the reactor components 106 via the connections 208 before products 103 exit via the reactor exit 105. Apart from the reactor entrance 104 and the reactor exit 105, it is preferred for the assembly of reactor housings 207 and connections 208 to be airtight.

Figure 3:
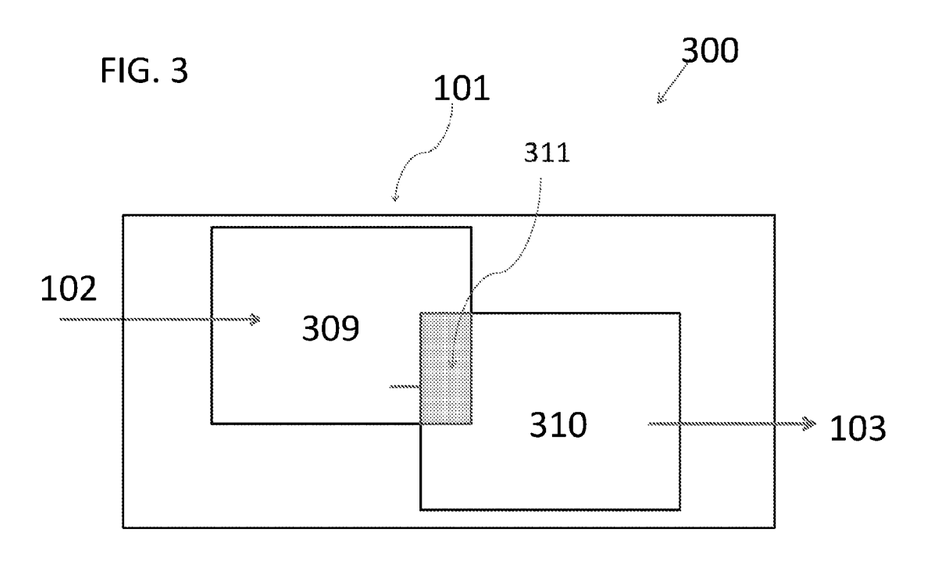
FIG. 3 shows a schematic view of a reactor in which there is at least partial spatial overlap of plasma source and catalyst.

FIG. 3 shows a schematic view of a reactor 300 in which there is at least partial overlap 311 between the plasma source 309 and the catalyst 310. For illustrative purposes, no further reactor components have been shown. Reactants 102 enter the reactor housing 101 and reaction material passes through the plasma source 309 and then the catalyst 310 before products 103 leave the housing 101. The spatial overlap 311 of the plasma source 309 and the catalyst 310 may be partial or complete.

Figure 4:
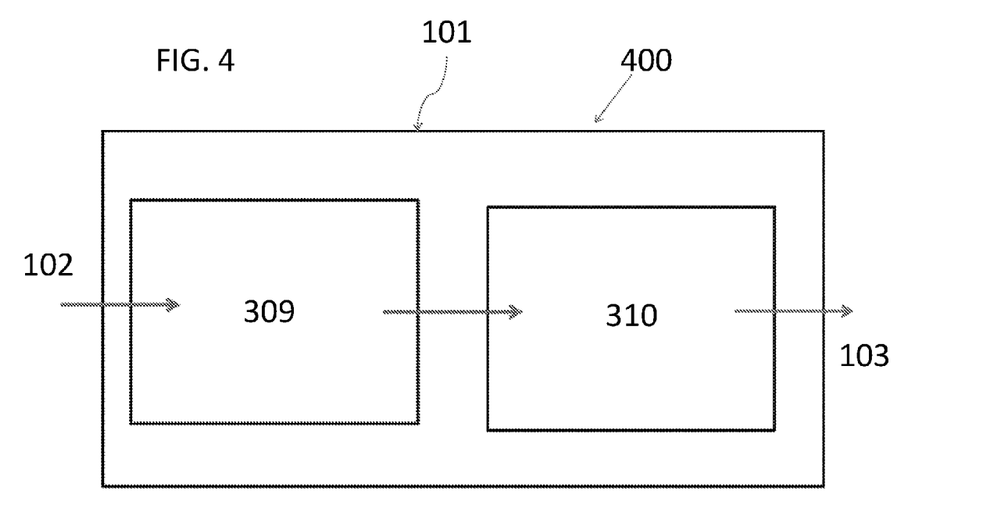
FIG. 4 shows a schematic view of a reactor in which there is no spatial overlap of plasma source and catalyst.

FIG. 4 shows a schematic view of a reactor 400 in which there is at no overlap between the plasma source 309 and the catalyst 310. For illustrative purposes, no further reactor components have been shown. Reactants 102 enter the reactor housing 101 and reaction material passes through the plasma source 309 and then the catalyst 310 before products 103 leave the housing 101.

Figure 5:
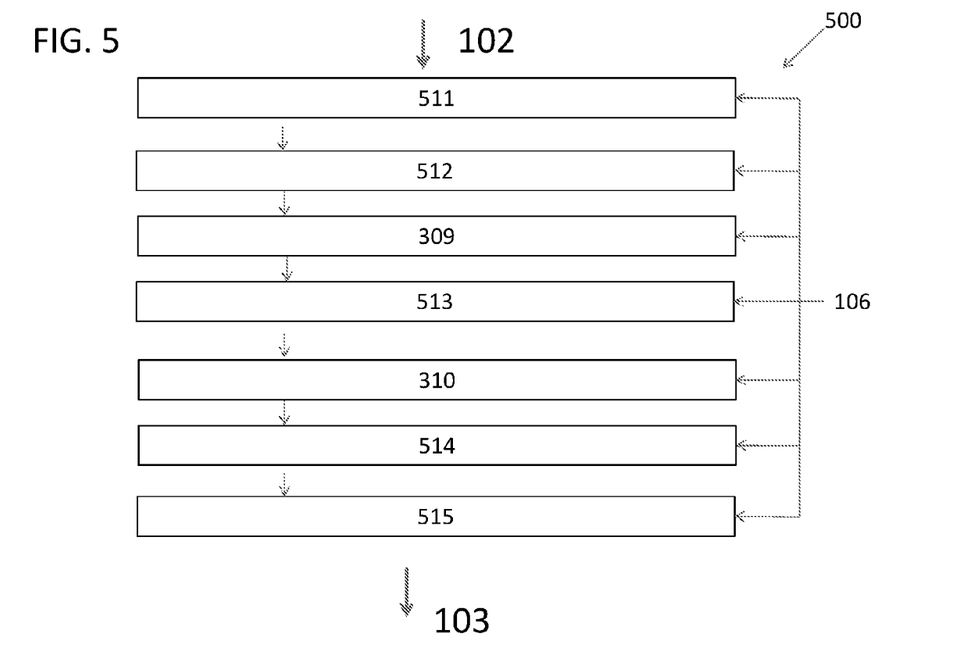
FIG. 5 shows a process flow for a reactor comprising further reactor components.

FIG. 5 shows a schematic process flow 500 for the process according to the invention. For the sake of illustration, a number of optional reactor components 106 are included. In order from upstream to downstream, reactants 102 enter the reactor and reaction material passes through; an optional reactant source component 511, preferably a crude oil cracker; an optional a pre-treatment component 512, preferably a dehumidifier and oxygen scrubber; a plasma source 309, preferably a non-thermal plasma source; an optional intermediate treatment component 513, preferably a carbon scrubber; a catalyst 310 comprising a catalyst metal, preferably Pd, on a mesoporous catalyst support material, preferably mesoporous silica; an optional post-treatment component 514, preferably a distillation component; and an optional downstream processing component 515, preferably a polymerization reactor; before products 103, preferably ethene or polythene, exit the reactor. One or more individual optional components can be omitted, more than one from each type of component may be employed, or even further components not shown can be employed. Options for providing reactor components in a single housing or as modules, and for providing at least partial, entire, or no overlap, are illustrated in the previous four figures. These options can also be combined.

Figure 6:
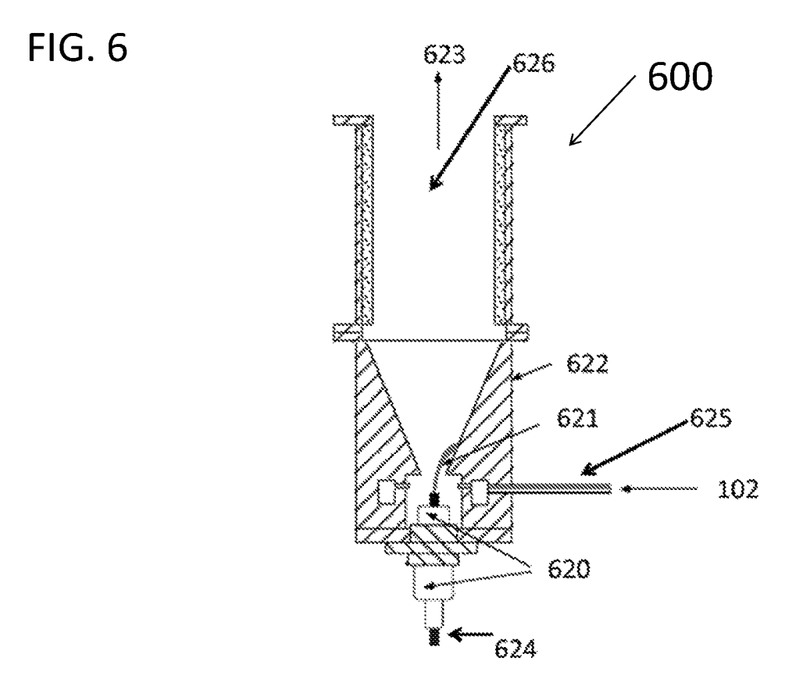
FIG. 6 shows a schematic view of a plasma source as employed in the examples.

FIG. 6 shows a schematic view of a plasma source 600 as employed in the examples. Reactant 102 enters the plasma source 600 via an inlet 625 and is exposed to a discharge 621 between an electrode 624 and a ground electrode 622. The electrode 624 is secured by insulators 620. The reactive species 623 produced by the plasma source 600 exit via the outlet 626.

FIG. 7 shows a process flow for an example preparation of a mesoporous support material with catalyst metal, in which the catalyst metal is introduced subsequent to the preparation of the mesoporous support material. The method is described in detail in example 1 below.

Test Methods

Specific Surface Area

BET measurements to determine specific surface area were made in accordance with DIN ISO 9277:1995. Alpha Aluminium oxide was used as reference. Filler rods were employed to reduce dead volume. Dead volume was determined using Helium gas (He 4.6). Nitrogen gas ($N_2$ 5.0) with a molecular cross-sectional area of 0.162 square nanometers ($nm^2$) at 77 Kelvins (K.) was used for the adsorption measurements. A Gemini 2360 (from Micromeritics) was employed for measurement. The specific surface area was given in $m^2/g$.

Pore Size

The average pore size was measured as the peak value on the pore size distribution (PAD), which was calculated from the adsorption branch as described above for specific surface area using the KJS (Ka-uk, Jaroniec, Sayari) method as described in M. Kruk, M. Jaroniec, A. Sayari, Langmuir, 13 (1997) 6267.

EXAMPLES

Example 1

Paladium catalyst mounted on SBA-15 mesoporous support material was prepared according to the following method:

The following apparatus was employed:
Digital weighing machine (AT 400, Metler Toledo)
Magnetic hot plate and stirrer (SLR, Schott)
Digital hot plate and stirrer (SLR, Schott)
Furnace (ELF10/6, Carbolite)
Microfiber filter (9134-ah)
Oven (ED53, Binder)
Desiccator
pH meter (CG842, Schott)
Autoclave reactor was used in the stage of hydrothermal treatment The steps are as follows:
1. a. Surfactant —$HO(CH_2CH_2O)_{20}(CH_2CH(CH_3)O)_{70}(CH_2CH_2O)_{20}H$, obtained from BASF SE under the trade name Pluronic P123 (0.845 g) was dissolved in 60 milliliters (mL) distilled water to form a clear solution.
   b. $Na_2SiO_4$ (based on 1 mole Silica) was added to the surfactant and then mixed until homogeneity was attained.
   c. 4 molar aqueous HCl solution (5.6 mL) was added to the mixture and stirred at about 30° C. to about 50° C. The mixture was stirred for 24 hours (hrs) using a magnetic hot plate and stirrer (ii above).
2. Following the above, the solution was transferred into a Teflon-lined autoclave and statically heated at 100° C. autogenously for 24 hrs.
3. Solid product was washed with distilled water and filtered and dried at 140° C. for 3 hrs in the above oven.
4. Calcination was followed in the furnace (ELF 10/6), at a temperature of about 500° C. to about 600° C. to remove the organic template and obtain SBA-15.
5. Pd from palladium acetylacetone solution dissolved in benzene was slowly added to the SBA-15 powder using the wetness impregnation method.
6. Stirring, preferably for about 1 hour, at a temperature of about 20° C. to about 30° C.
7. Followed by Drying at 120° C. for 24 hrs and the calcination between 500°-600° C. for 4 hrs to obtain the mesoporous support material with catalyst metal.

Example 2

A reactor was provided by connecting the following components in flow communication: a pressurised cylinder containing natural gas (greater than or equal to 99% wt. % methane), purchased from Sigma Aldrich; a valve and pressure regulator provided with the gas cylinder, a flow rate meter, a plasma source apparatus as displayed schematically in FIG. 6, a 4 tube catalyst container packed with Pd supported on SBA-15 as prepared in Example 1, and an HP M200D gas chromatograph. Connections between the reactor parts were made using rubber tubing so as to be airtight. Pressure of the natural gas furnished from the regulator was modified so as to achieve a flow rate of 40 liters per minute (L/min). The specific power consumption of the plasma source, expressed as power consumption per unit weight of methane flow was calculated as 0.8 kW/g. The plasma source was operated in AC mode with a frequency of 100 Hertz (Hz), and a voltage of 2000 Volts (V). Yield of ethene, hydrogen and by-products was measured at state of steady flow using the gas chromatograph.

Comparative Example

A reactor was provided and a flow reaction carried out and analysed as in example 2 with the exception that Pd mounted on Pentasil-zeolite with the formula $Na_nAl_nSi_{96-n}O_{192} \cdot 16H_2O$ with n=12 was employed in place of Pd supported on SBA-15. Reaction yields by weight as listed in FIG. 2 were described using the following scale: -- very low, - low, o medium, + high, ++ very high.

TABLE 1

| Mesoporous support materials employed | | | |
|---|---|---|---|
| Example | Support | $d_{90}$ pore size [nm] | Specific surface area [$m^2/g$] |
| 2 | SBA-15 (mesoporous) | 7.6 | 530 |
| Comparative | Pentasil-zeolite (microporous) | 0.55 | 85 |

TABLE 2

| Reaction Yields | | | | | |
|---|---|---|---|---|---|
| Example | Yield $C_2H_4$ | Yield $C_2H_2$ | Yield $C_2H_6$ | Yield $H_2$ | Yield C |
| 2 | ++ | -- | -- | ++ | -- |
| Comparative | o | - | - | ○ | - |

The reactor and processes disclosed herein include at least the following embodiments:

Embodiment 1

A reactor comprising as reactor parts: a. a housing; and in said housing; b. a plasma source; and c. a catalyst, wherein said catalyst comprises as catalyst parts: i) a mesoporous support; ii) a metal selected from the group Pd, Ni, Ag or at least two thereof, wherein the metal is carried by said mesoporous support; wherein at least a part of said plasma source is located in said housing upstream of said catalyst.

Embodiment 2

The reactor according to embodiment 1, wherein the mesoporous support has a $d_{50}$ value for pore diameter of about 2 to about 50 nm.

Embodiment 3

The reactor according to embodiment 1 or 2, wherein the mesoporous support is mesoporous silica.

Embodiment 4

The reactor according to any of the previous embodiments, wherein the mesoporous support has a surface area to mass ratio of about 10 to about 1500 m$^2$/g.

Embodiment 5

The reactor according to any of the preceding embodiments, wherein the metal in the catalyst is Pd.

Embodiment 6

The reactor according to any of the previous embodiments wherein the mesoporous support is selected from one of the following families: SBA-15, SBA-16, MCM-48, MCM-41, or a combination of at least two thereof.

Embodiment 7

The reactor according to any of the preceding embodiments, wherein the catalyst comprises Pd supported on SBA-15, SBA-16, MCM-48, MCM-41, or a combination of at least two thereof.

Embodiment 8

The reactor according to any of the preceding embodiments, wherein the mesoporous support is SBA-15.

Embodiment 9

The reactor according to any of the preceding embodiments, wherein there is at least partial spatial overlap of the plasma source and the catalyst.

Embodiment 10

The reactor according to any of the preceding embodiments, wherein there is no spatial overlap of the plasma source and the catalyst.

Embodiment 11

A process for the preparation of a product selected from ethene and hydrogen or both comprising: i. feeding methane into a reactor according to any of the preceding embodiments; and ii. reacting the methane to furnish the product in the reactor.

Embodiment 12

The process according to embodiment 11, wherein methane is fed to the reactor mixed with a carrier gas selected from the group consisting of N$_2$, Ar, or He, or a combination of at least two thereof.

Embodiment 13

The process according to embodiment 11 or 12, wherein at least one of the following conditions is satisfied: a. the maximum temperature within the reactor is about 0 to about 200° C.; b. the partial pressure of methane fed to the reactor is about 0.5 to about 2 atm.; c. the power density of the plasma source output, expressed as the power of the plasma source divided by the flow rate of the methane, is about 0.1 to about 30 kJ/g; d. the partial pressure of the carrier gas is about 0.1 to about 10 atm.

Embodiment 14

A process for the preparation of a downstream product comprising: i. preparation of ethene by a process according to any of the embodiments 11 to 13; ii. reaction of the ethene to form the downstream product.

Embodiment 15

The process according to embodiment 14, wherein the downstream product is a polymer.

Embodiment 16

The process according to embodiment 14 or 15, wherein the downstream product is a polythene.

Embodiment 17

The process according to any of the embodiments 14 to 16, wherein the downstream product is converted into a shaped body.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to distinguish one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

All cited patents, patent applications, and other references are incorporated herein by reference in their entirety. However, if a term in the present application contradicts or conflicts with a term in the incorporated reference, the term from the present application takes precedence over the conflicting term from the incorporated reference. While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A reactor comprising as reactor parts:
   a housing; and in said housing;
   a plasma source; and
   a catalyst, wherein said catalyst comprises as catalyst parts:
      a mesoporous support;
      a metal comprising Pd, wherein the metal is carried by said mesoporous support;
      wherein at least a part of said plasma source is located in said housing upstream of said catalyst,
      wherein the Pd is supported on SBA-15, SBA-16, MCM-48, MCM-41, or a combination of at least two thereof.

2. The reactor according to claim 1, wherein the mesoporous support is SBA-15.

3. The reactor according to claim 1, wherein the reactor comprises a reactor entrance and a reactor exit, and wherein said plasma source is located near said reactor entrance and said catalyst is located near said reactor exit.

4. The reactor according to claim 1, wherein the mesoporous support has a $d_{50}$ value for pore diameter of about 2 to about 50 nm.

5. The reactor according to claim 1, wherein the mesoporous support has a surface area to mass ratio of about 10 to about 1500 $m^2/g$.

6. The reactor according to claim 1, wherein there is at least partial spatial overlap of the plasma source and the catalyst.

7. The reactor according to claim 1, wherein there is no spatial overlap of the plasma source and the catalyst.

8. A process for the preparation of a product selected from ethene hydrogen or both comprising:
   feeding methane into a reactor according to claim 1; and
   reacting the methane to furnish the product in the reactor.

9. The process according to claim 8, wherein methane is fed to the reactor mixed with a carrier gas selected from $N_2$, Ar, He, or a combination of at least two thereof.

10. The process according to claim 8, wherein at least one of the following conditions is satisfied:
    a. the maximum temperature within the reactor is about 0 to about 200° C.;
    b. the partial pressure of methane fed to the reactor is about 0.5 to about 2 atm;
    c. the power density of the plasma source output, expressed as the power of the plasma source divided by the flow rate of the methane, is about 0.1 to about 30 kJ/g;
    d. the partial pressure of the carrier gas is about 0.1 to about 10 atm.

11. A process for the preparation of a downstream product comprising:
    preparation of ethene by a process according to claim 8; and
    reaction of the ethene to form the downstream product.

12. The process according to claim 8, wherein the downstream product is a polymer.

13. The process according to claim 8, wherein the downstream product is a polythene.

14. The process according to claim 8, wherein the downstream product is converted into a shaped body.

* * * * *